(12) United States Patent
Ishizuka

(10) Patent No.: US 6,886,562 B2
(45) Date of Patent: May 3, 2005

(54) OXYGEN BREATHING APPARATUS

(75) Inventor: Muneyuki Ishizuka, 2-8-18 Ooyamaguti, Siroi-City, Chiba Pref, 270-1434 (JP)

(73) Assignees: Muneyuki Ishizuka, Siroi (JP); Leslie W. Peterson, Castle Rock, CO (US); Peter Durante, Aurora, CO (US)

( * ) Notice: Subject to any disclaimer, the term of this patent is extended or adjusted under 35 U.S.C. 154(b) by 0 days.

(21) Appl. No.: 10/611,165

(22) Filed: Jun. 30, 2003

(65) Prior Publication Data

US 2004/0050390 A1 Mar. 18, 2004

(30) Foreign Application Priority Data

Sep. 13, 2002 (JP) ......................................... 2002-268027

(51) Int. Cl.$^7$ ............................................. A61M 16/00
(52) U.S. Cl. ............................... 128/206.11; 128/206.18
(58) Field of Search ....................... 128/203.22, 203.18, 128/204.11, 204.12, 206.11, 206.13, 206.15, 206.18, 207.17, 207.18, 846, 847, 857, 858; 351/156–158; 2/437, 438, 171.3

(56) References Cited

U.S. PATENT DOCUMENTS

| | | | | |
|---|---|---|---|---|
| 2,168,705 A | * | 8/1939 | Charles et al. | 128/207.18 |
| 3,209,755 A | * | 10/1965 | McCarthy et al. | 604/174 |
| 4,195,918 A | * | 4/1980 | Freche et al. | 351/158 |
| 4,465,067 A | * | 8/1984 | Koch et al. | 128/207.18 |
| 4,559,941 A | | 12/1985 | Timmons et al. | 128/207.18 |
| 4,708,446 A | | 11/1987 | Timmons et al. | 351/158 |
| 4,858,476 A | * | 8/1989 | Tobin | 73/863.23 |
| 4,996,983 A | * | 3/1991 | AmRhein | 128/206.11 |
| 5,193,534 A | * | 3/1993 | Peppler | 128/207.18 |
| 5,368,582 A | * | 11/1994 | Bertera | 604/295 |
| 5,438,979 A | * | 8/1995 | Johnson et al. | 128/207.18 |
| 6,409,338 B1 | * | 6/2002 | Jewell | 351/158 |
| 6,439,235 B1 | * | 8/2002 | Larquet et al. | 128/207.18 |
| 6,772,762 B2 | * | 8/2004 | Piesinger | 128/847 |
| 2004/0035431 A1 | * | 2/2004 | Wright | 128/207.18 |
| 2004/0074500 A1 | * | 4/2004 | DePuy | 128/207.18 |

OTHER PUBLICATIONS

Paolo Moriachhi, Oxygen–Therapy Frames, Vsision Stores, Italy.
Glasses for Oxygen Therapy, Vivisol, Salter Labs of Arvin, CA.

* cited by examiner

*Primary Examiner*—Henry Bennett
*Assistant Examiner*—Teena Mitchell
(74) *Attorney, Agent, or Firm*—Sheridan Ross P.C.

(57) ABSTRACT

An oxygen breathing apparatus with a spectacle kit comprising a plurality of frame members of eyeglasses, such as a tubular temple member an tubular endpiece member, and a hinged joint through which the tubular members are rotatably and hermetically connected with each other to establish a common joint portion of these tubular members By providing a thick-walled connection portion in each of the tubular members, the apparatus is free from any deformation of the common joint portion of the tubular members even when folding/unfolding operation of the temple member is repetitively performed.

13 Claims, 6 Drawing Sheets

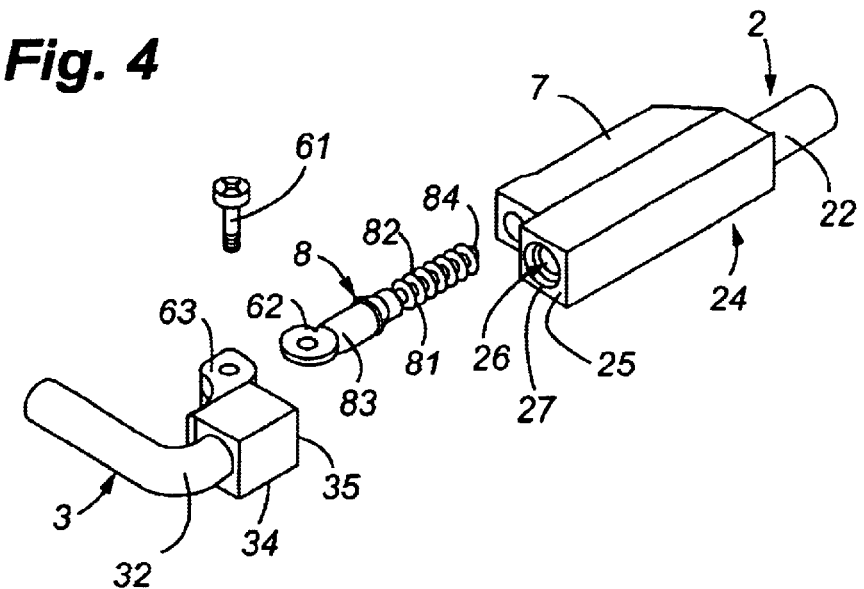
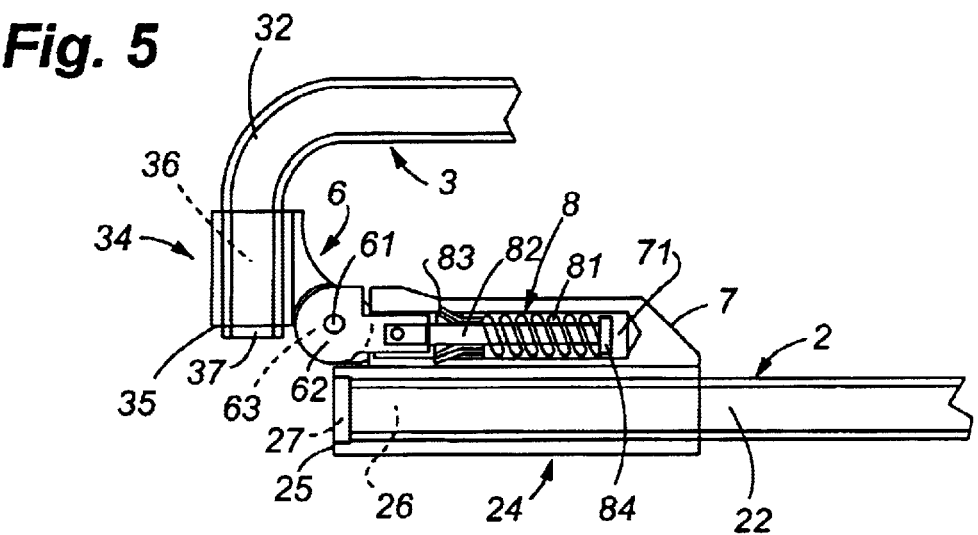

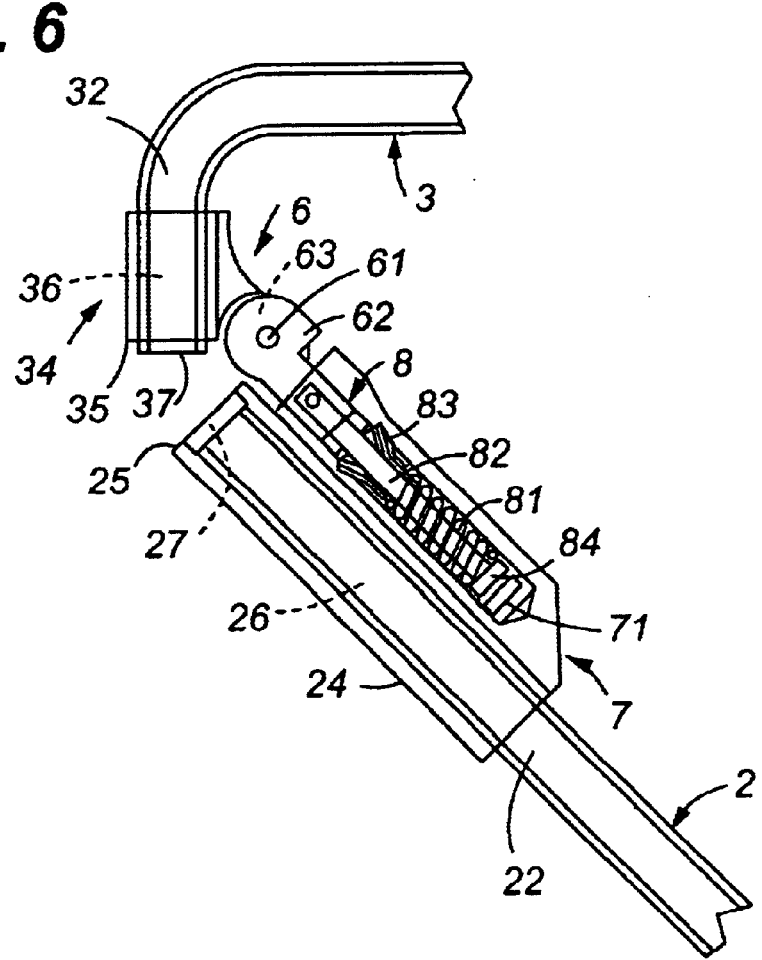

OXYGEN BREATHING APPARATUS

BACKGROUND OF THE INVENTION

1. Field of the Invention

The present invention relates to an oxygen breathing apparatus used to deliver oxygen to a person having lungs of limited capacity due to lung damage which require supplemental oxygen to assist in everyday life, wherein oxygen is supplied from an oxygen supply source such as an oxygen concentrator, a compressed oxygen supply tank and the like to nostrils of the person through a pair of cannulas (i.e., medical tubular members). More particularly, the present invention relates to such an oxygen breathing apparatus, which is integrally formed with a spectacle kit (i.e., eyeglasses) to assume a spectacle shape in appearance, and is substantially free from any deformation of a common joint portion (described later) of the spectacle kit.

2. Description of the Related Art

Heretofore, it has been known to provide a spectacle-shaped oxygen breathing apparatus, which is excellent in appearance and capable of steadily supplying oxygen to a person wearing the breathing apparatus without any fear that a pair of cannulas having been inserted into nostrils of the person drop out of the nostrils in use.

Such a conventional spectacle-shaped oxygen breathing apparatus is shown in FIGS. 8 and 9. As is clear from these drawings, the spectacle kit of the conventional breathing apparatus has some or all of its frame members constructed of tubular members to permit its temple members 2 and its corresponding end piece members 3 to air-communicate with each other. As shown in FIG. 8, as to the spectacle kit, an opening end portion 21 of the temple member 2 is hermetically connected with a small-diameter cannula 4 which extends from an oxygen supply source (not shown). On the other hand, the end piece member 3 has its opening end portion 31 hermetically connected with a nostril cannula 5. The breathing apparatus is easy in wearing, and excellent in appearance when worn by a person. Further, in the spectacle kit of the apparatus, as shown in FIG. 9, the temple members 2 are connected with the end piece members 3 through hinged joints 6. This makes it possible for the person wearing the breathing apparatus to fold the apparatus during non-use thereof. The thus folded apparatus is capable of reducing its size to realize easy storage of the apparatus. This is very advantageous to the person using the breathing apparatus.

In the hinged joints 6 of the spectacle kit, as is clear from FIG. 9, the tubular endpiece member 3 is rotatably connected with the corresponding tubular temple members 3. During non-use of the breathing apparatus, when the temple members 2 of the spectacle kit are unfolded, a sleeve-like insertion convex portion 33 of each endpiece member 3 is hermetically inserted into an open end portion 22 of the corresponding temple member 2, which enables oxygen to be transferred from the temple member 2 to the endpiece member 3 of the spectacle kit without any leakage of oxygen.

However, the conventional breathing apparatus suffers from the following problems, which will be now described in detail.

It is necessary for the breathing apparatus to supply oxygen, at a relatively small constant rate, from the oxygen supply source (not shown) to the nostril cannulas 5. Due to this, each of the endpiece members 3 and the temple members 2 is constructed from a small-diameter tubular member, a diameter of which is substantially equal to that of the small-diameter cannula 4. Further, in order to keep excellencies of the breathing apparatus in appearance, weight and fittingness, the small-diameter cannula 4 is constructed of a tubular member with the thinnest possible wall thickness.

Due to this, the open end portion 22 of the temple member 2, into which the sleeve-like convex portion 33 of the endpiece member 3 is hermetically inserted, is also thin in wall thickness. Consequently, in inserting the sleeve-like convex portion 33 of the endpiece member 3 into the open end portion 22 of the temple member 2, the sleeve-like convex portion 33 of the endpiece member 3 is brought into frictional contact with the open end portion 22 of the temple member 2. When such frictional contact is repeatedly performed in use, a stop screw 61 of the hinged joint 6, through which the endpiece member 3 is rotatably connected with the temple member 2, is often loosened. When the stop screw 61 is loosened, as is clear from FIG. 9, the open end portion 22 of the temple member 2 is flared outwardly to cause oxygen leakage. There is also a fear that the sleeve-like convex portion 33 of the endpiece member 3 is deformed or battered down to prevent passage of oxygen through the portion 33. The above troubles in passage of oxygen make it impossible for the breathing apparatus to supply oxygen to the person at a necessary rate prescribed by a doctor in charge, which often leads to the person's anoxia such as cyanosis and like damages.

SUMMARY OF THE INVENTION

Under such circumstances, the present invention was made to solve the problems inherent in the prior art. Consequently, it is an object of the present invention to provide a spectacle-shaped oxygen breathing apparatus which is free from any deformation of the common joint portion of a spectacle kit used in the apparatus.

In accordance with the present invention, the above object is accomplished by providing:

In an oxygen breathing apparatus provided with a spectacle kit, wherein: the spectacle kit is constructed of a plurality of frame members of eyeglasses, some or all of which members are constructed of hollow tubular members; the frame members comprises an end piece member (3) and a temple member (2); the end piece member (3) is in air communication with the temple member (2); the temple member (2) has one (21) of a pair of its opposite open end portions (21,22) in air communication with a cannula (4) connected with an oxygen supply source; the end piece member (3) has one (31) of a pair of its opposite open end portions (31, 32) in air communication with a nostril cannula (5); and, the temple member (2) is rotatably connected with the end piece member (3) through a hinged joint (6), characterized in that:

each of the temple member (2) and the endpiece member (3) has the other (22, 32) of their opposite open end portions, which is adjacent to the hinged joint (6), constructed of a thick-walled connection portion (24, 34) provided with a contact end surface (25, 35);

the thick-walled connection portion (24) of the temple member (2) is provided with a concave portion (27);

the thick-walled connection portion (34) of the endpiece member (3) is provided with a convex portion (37) which is hermetically received in the concave portion (27) of the temple member (2) in an insertion manner to establish air-communication between the temple member (2) and the endpiece member (3) when the contact end surfaces (25, 35) of both the temple member (2) and the endpiece member (3) are brought into press-contact with each other to form a common joint portion (27, 37) of the tubular members (2, 3);

whereby the common joint portion (27, 37) of the tubular members (2, 3) is prevented from being damaged in use.

In the oxygen breathing apparatus having the above construction, preferably the hinged joint (6) is of a spring-biased type.

The hinged joint of such a spring-biased type makes it possible for the person to perform folding/unfolding operation of the temple member (2) of the spectacle kit in an easy and steady manner, without damaging the common joint portion (27, 37) of these tubular members (2, 3). Particularly, in unfolding the temple member (2), a biasing force exerted by the hinged joint (6) of the spring-biased type may forcibly keep the common joint portion (27, 37) of these tubular members (2, 3) in an air-tightly sealed state, which ensures a steady and constant supply of oxygen at a prescribed rate to the person wearing the oxygen breathing apparatus of the present invention.

BRIEF DESCRIPTION OF THE DRAWINGS

The above and other objects, advantages and features of the present invention will be more apparent from the following description taken in conjunction with the accompanying drawings in which:

FIG. 4 is an exploded perspective view of an alternative embodiment of the essential part of the breathing apparatus of the present invention shown in FIGS. 2 and 3;

FIG. 5 is a plan view of a further partially broken essential part of the oxygen breathing apparatus, illustrating the folded state of the spectacle kit of the apparatus of the present invention shown in FIG. 4;

FIG. 6 is a plan view of a further partially broken essential part of the oxygen breathing apparatus, illustrating the unfolded state of the spectacle kit of the apparatus of the present invention shown in FIG. 4;

DETAILED DESCRIPTION OF THE PREFERRED EMBODIMENTS

The best modes for carrying out the present invention will be described in detail using embodiments of the present invention with reference to the accompanying drawings.

Figure 1:
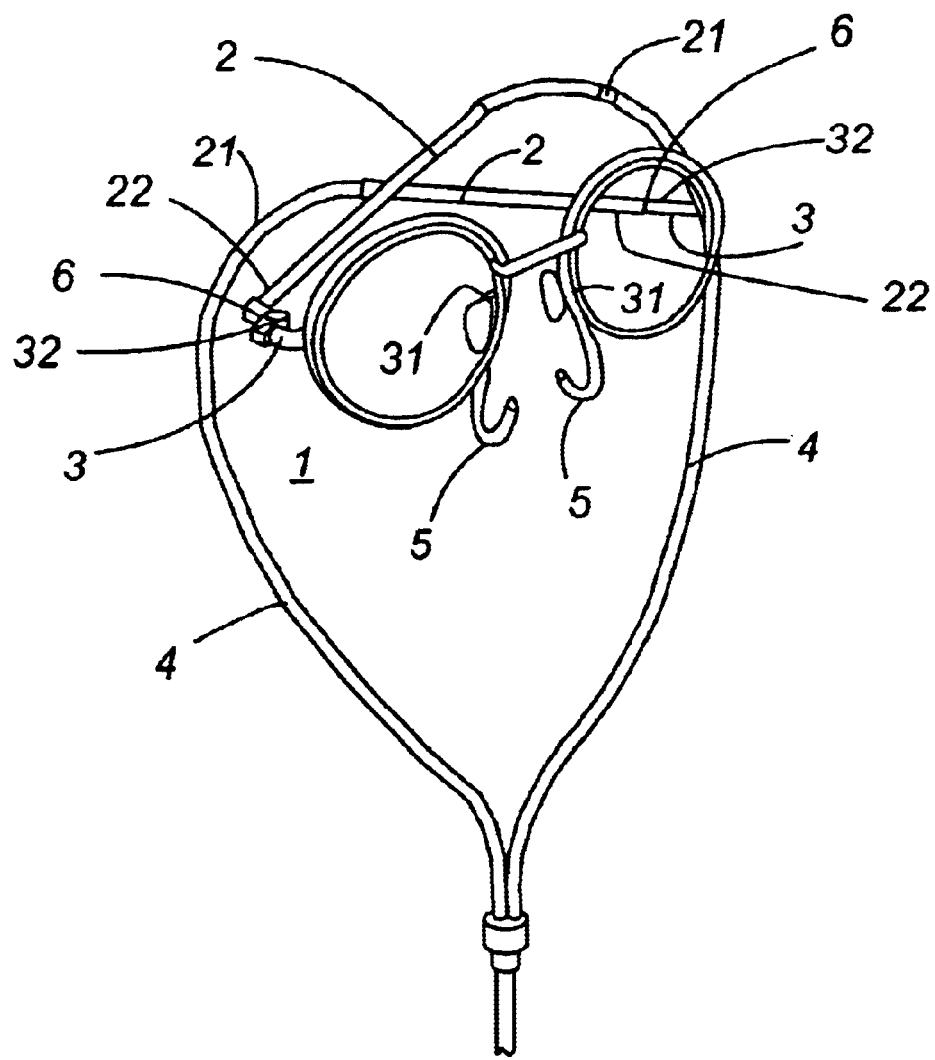
FIG. 1 is a perspective view of an embodiment of the oxygen breathing apparatus of the present invention.
Figure 2:
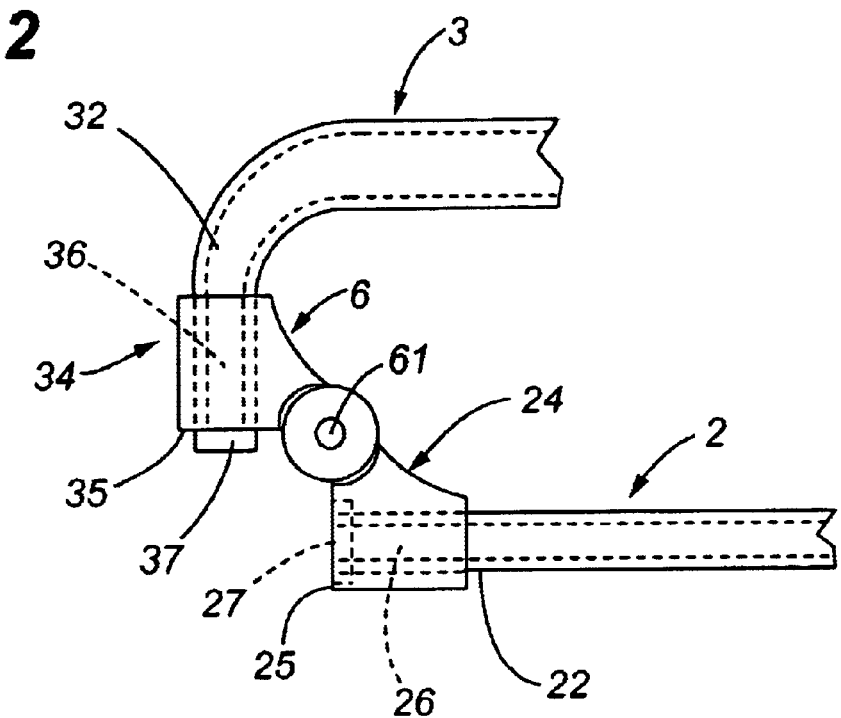
FIG. 2 is a plan view of a partially broken essential part of the oxygen breathing apparatus, illustrating a folded state of the spectacle kit of the apparatus of the present invention shown in FIG. 1.
Figure 3:
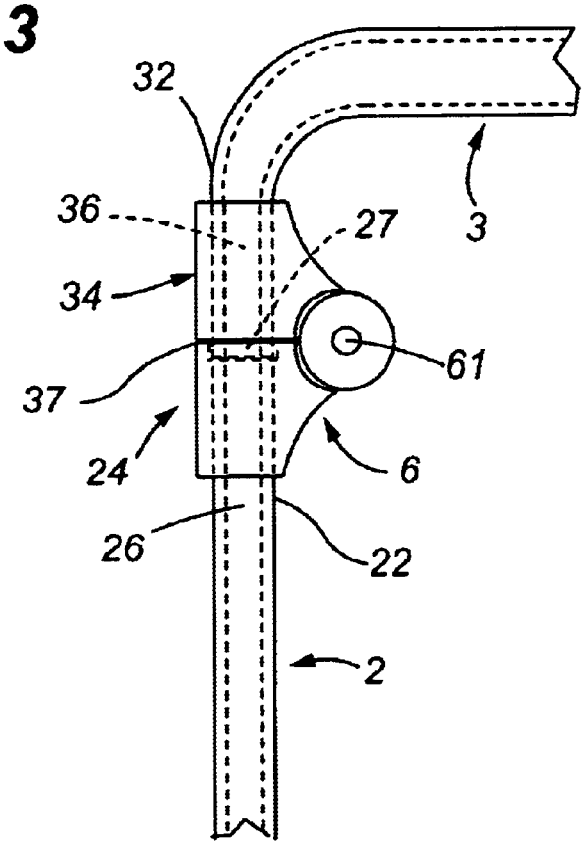
FIG. 3 is a plan view of a partially broken essential part of the oxygen breathing apparatus, illustrating an unfolded state of the spectacle kit of the apparatus of the present invention shown in FIG. 1.

FIGS. 1 to 3 show a first embodiment of an oxygen breathing apparatus of the present invention, which is substantially similar in construction to a conventional one with the exception of an essential part of the first embodiment of the present invention.

As is clear from FIG. 1, some or all of a plurality of frame members of a spectacle kit (i.e., eyeglasses) of the oxygen breathing apparatus of the present invention are constructed of hollow tubular members, including a pair of temple members 2 and a pair of end piece members 3. Each temple member 2 is in air communication with each end piece member 3.

In the embodiment shown, the open end portion 21 of the temple member 2 is in air communication with a cannula 4 connected with an oxygen supply source (not shown). On the other hand, the end piece member 3 is in air communication with a nostril cannula 5 through open end portion 31. Supplying oxygen through both temple members and end piece members provides the most oxygen supply to the user.

The temple member 2 is rotatably connected with the end piece member 3 through a hinged joint 6. More particularly, as shown in FIG. 2, the temple member 2 is provided with a thick-walled connection portion 24. This connection portion 24 is provided with a contact end surface 25 and a hollow section 26 which is in air communication with the opposite end portion 22 through the temple member 2.

On the other hand, the end piece member 3 is provided with a contact end surface 35 and a thick-walled connection portion 34. The connection portion 34 is provided with a hollow section 36. This hollow section 36 is in air communication with both the opposite end portion 31 through the end piece member 3 and the corresponding hollow section 26 of the eyepiece member 2 when the tubular member 2 is in an unfolded state, as shown in FIG. 3.

The thick-walled connection portion 34 of the end piece member 3 is disposed adjacent to the hinged joint 6 and provided with a convex portion 37 extending axially outward. On the other hand, the thick-walled connection portion 24 of the temple member 2 is provided with a concave portion 27 which is capable of hermetically receiving therein the insertion convex portion 37 of the end piece member 3 in an insertion manner to establish air-communication between the temple member 2 and the end piece member 3 when the contact end surfaces 25, 35 of both the temple member 2 and the end piece member 3 are brought into press-contact with each other to form a "common joint portion (27, 37)" of these members 2, 3.

There is substantially no difference between the apparatus of the present invention and the conventional one in construction with the exception of the "common joint portion (27, 37)" of the present invention. Due to the presence of the concept of the "common joint portion (27, 37)" of the present invention, the apparatus of the present invention is improved in reliability relative to the conventional apparatus, because it is possible for the apparatus of the present invention to supply oxygen to a person wearing the apparatus in a steady manner without fail due to the provision of the "common joint portion (27, 37)", which is constructed of both the convex portion 37 of the end piece member 3 and the corresponding concave portion 27 of the temple member 2 capable of hermetically receiving therein the convex portion 37 of the end piece member 3 in an insertion manner in a condition in which the contact end surfaces 25, 35 are brought into direct press-contact with each other.

More specifically, in the apparatus of the present invention, when the convex portion 37 of the thick-walled connection portion 34 of the end piece member 3 is inserted into the corresponding concave portion 27 of the temple member 2, the contact end surfaces 25 of the temple member 2 is brought into direct press-contact with the corresponding contact end surface 37 of the end piece member 3 without having the convex portion 37 of the end piece member. 3 brought into direct-contact with the corresponding concave portion 27 of the temple member 2. Due to this, in the apparatus of the present invention, there is no fear that the concave portion 27 of the temple member 2 is deformed or outwardly flared by repeated insertion of the corresponding convex portion 37 of the end piece member 3 into the concave portion 27 of the temple member 2 in use. This contributes remarkably to prevention of loosening of the stop screw 61 of the hinged joint 6 and therefore to improvement of the apparatus of the present invention in reliability.

In the first embodiment of the present invention, as is clear from FIGS. 2 and 3, each of the hollow sections 26, 36 of the thick-walled connection portions 24, 34 of the frame members 2, 3 of the spectacle kit is equal in inner diameter to each of the temple member 2 and the endpiece member 3. Consequently, there is no fear that these hollow sections 26, 36 prevent oxygen from steadily flowing through the apparatus.

FIGS. 4 to 7 show a second embodiment of the apparatus of the present invention, which is substantially similar in construction to the first embodiment shown in FIGS. 1 to 3, with the exception of an essential part of the second embodiment. The essential part of the second embodiment resides in the hinged joint 6, which is of a spring-biased type of this second embodiment.

More specifically, as is in the case of die first embodiment shown in FIGS. 1 to 3, the temple member 2 and the end piece member 3 are rotatably connected with each other through the hinged joint 6, wherein the stop screw 61 of the hinged joint 6 passes through the thick-walled connection portions 24, 34 of the temple member 2 and the end piece member 3 to rotatably connect these portions 24, 34 with each other through the stop screw 61. The contact end surface 35 of the end piece member 3 extends in a direction perpendicular to a longitudinal direction of the end piece member 3. Extended outward in the longitudinal direction of the end piece member 3 from the contact end surface 35 is the convex portion 37, a hollow section of which communicates with the hollow section 36 of the thick-walled portion of the end piece member 3. The convex portion 37 of the end piece member 3 is hermetically fitted in the concave portion 27 of the temple member 2 in an insertion manner when the temple member 2 is unfolded. In the thick-walled portion 24 of the temple member 2, the concave portion 27 is in air communication with the hollow section 26 of the temple member 2. Consequently, as is clear from FIG. 7, when the convex portion 37 of the end piece member 3 is hermetically fitted in the concave portion 27 of the temple member 2 in an insertion manner, the hollow section 36 of the end piece member 3 is in air communication the hollow section 26 of the temple member 2.

As shown in FIGS. 4 to 7, the thick-walled connection portion 24 of the temple member 2 assumes a substantially rectangular shape, and is provided with a spring storage portion 7 constructed of a longitudinal bore 71. As is clear from in FIG. 7, this longitudinal bore 71 of the thick-walled connection portion 24 extends in parallel with the temple member 2, and is opened at the front to the hinged joint 6 and closed at the rear to a distal end portion of the temple member 2. Loosely received in the longitudinal bore 71 of the thick-walled connection portion 24 of the temple member 2 is a spring unit 8.

Figure 7:
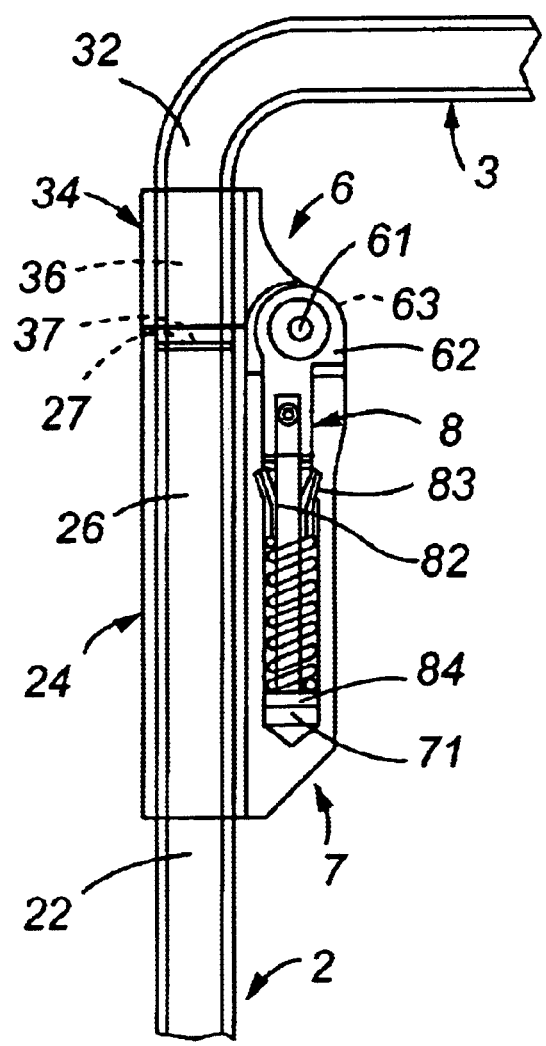
FIG. 7 is a plan view of a further partially broken essential part of the oxygen breathing apparatus, illustrating the frilly unfolded state of the spectacle kit of the apparatus of the present invention shown in FIG. 4.
Figure 8:
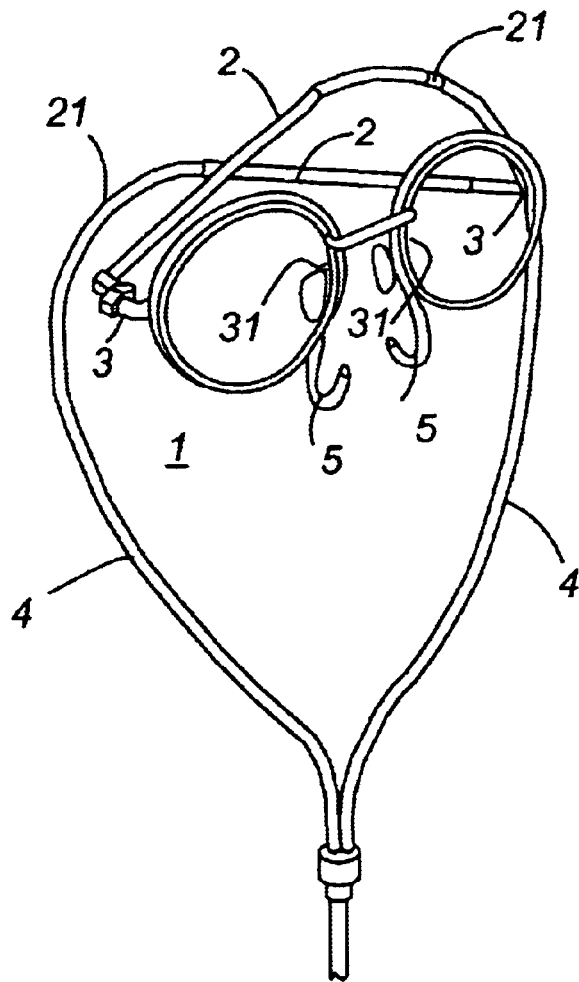
FIG. 8 is a perspective view of the prior art oxygen breathing apparatus.
Figure 9:
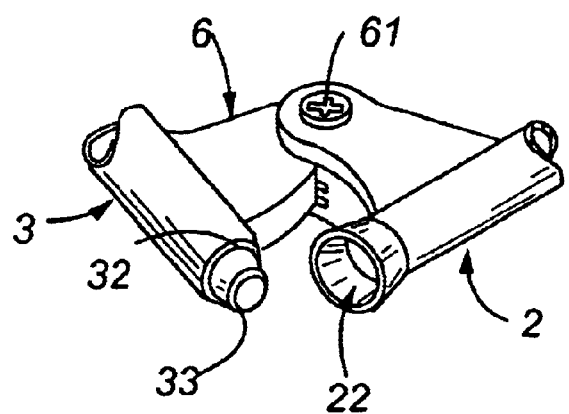
FIG. 9 is an enlarged perspective view of the hinged joint of the spectacle kit of the prior art oxygen breathing apparatus shown in FIG. 8.

As is clear from FIG. 4, the spring unit 8 is constructed of: a tension coil spring 81; a spring support member 82 provided with an elongated shank portion and a disc-like spring stop portion 84 fixedly mounted on the distal end portion of the elongated shank portion, on which shank portion the tension coil spring 81 is coaxially and axially slidably mounted; a fitting member 83 through which the elongated shank portion of the spring support member 82 is axially slidably received in the opening of the longitudinal bore 71 of the thick-walled connection portion 24 of the temple member 2; and, a hinge connection member 62, which is one of components of the hinged joint 6, as is clear from FIG. 4. As shown in FIG. 7, the disc-like stop portion 84 of the spring support member 82 is larger in outer diameter than the elongated shank portion of the same support member 82 and extends in a direction perpendicular to the longitudinal axis of the elongated shank portion. The tension coil spring 81 is axially movably mounted on the elongated shank portion of the spring support member 82 between the spring stop portion 84 of the spring support member 82 and the fitting member 83. As is clear from FIG. 7, this fitting member 83 assumes a wedge-like shape in cross section to steadily hold the spring support member 82 inside the spring storage portion 7 constructed of the longitudinal bore 71. In operation, under the influence of a resilient force exerted by the tension coil spring 81 of the hinged joint 6, the hinge connection member 62 fixedly mounted on a front end portion of the spring support member 82 is pulled back toward the bottom of the spring storage portion 7.

The hinge connection member 62 is rotatably connected with another hinge connection member 63 through the stop screw 61 of the hinged joint 6. Such another hinge connection member 63 is integrally formed with the thick-walled connection portion 34 of the endpiece member 3 to extend inwardly, as shown in FIG. 4.

In the second embodiment of the present invention having the above construction, as is in the case of the first embodiment shown in FIGS. 1 to 3, there is no fear that the concave portion 27 of the temple member 2 is deformed or outwardly flared by repeated insertion of the corresponding concave portion 37 of the endpiece member 3 into the concave portion 27 of the temple member 2 in use. As shown in FIG. 7, in unfolding the temple member 2, the endpiece member 3 is pulled back through the hinge members 62, 63 under the influence of a resilient force exerted by the tension coil spring 81, as described above, so that the convex portion 37 of the thick-walled connection portion of the endpiece member 3 is brought into contact with the corresponding concave portion 27 of the thick-walled connection portion 27 of the temple member 2. Due to this, there is no fear that the endpiece member 3 is disengaged from the temple member 2 in use. This ensures a steady supply of oxygen at a prescribed rate to the person wearing the oxygen breathing apparatus of the present invention, without fail.

Further, as is clear from the above description, the resilient force exerted by the tension coil spring 81 of the spring unit 8 may steadily hold the temple member 2 at either its folded state or its unfolded state. Due to this, the person may perform the folding and unfolding operation of the temple member 2 with less effort. The apparatus of the present invention is improved in repetitive accuracies in positioning when the temple member 2 is connected with the endpiece member 3, which may effectively reduce the possibility of loosening of the stop screw 61. Further, it is also possible for the apparatus of the present invention to have the temple member 2 unfolded further outwardly relative to the endpiece member 3 beyond its normal unfolded position. Also, in fittingness too, the apparatus of the present invention is improved. Since the resilient force exerted by the tension coil spring 81 of the spring unit 8 may steadily hold the temple member 2 at its folded state, there is no fear that the temple member 2 is accidentally unfolded during non-use of the apparatus. This facilitates storage of the apparatus during non-use of the apparatus.

The effects of the oxygen breathing apparatus will be now described.

As described above, in the apparatus of the present invention, there is no feat that the common joint portion (27, 37) formed between the endpiece member 3 and the temple member 2 are damaged or disconnected to cause leakage of oxygen in use. This ensures a steady supply of oxygen at a prescribed rate to the person wearing the apparatus of the present invention, without fail. Further, the apparatus of the present invention is also improved in reliability and in both the manufacturing cost and the maintenance cost.

The hinge joint 6 of the spring-biased type may effectively improve the apparatus of the present invention in reliability, fittingness and easiness in use.

What is claimed is:

1. In an oxygen breathing apparatus having a plurality of tubular frame members, the tubular frame members comprising first and second end piece members and first and second temple members, the end piece members and the temple members each having a first end and a second end, with the first end of at least one of the temple members in air communication with an oxygen supply and the first end of at least one of the end piece members in air communication with a nostril cannula, the second end of the first temple member rotatably hinged relative to the second end of the first end piece member and moveable between a first position and a second position, and the second end of the second temple member rotatably hinged relative to the second end of the second end piece member and moveable between a first position and a second position, the improvement comprising:

a. a thick walled connection portion disposed at the second end of each end piece member and each temple member, each of said thick walled portions comprising a contact end surface;

b. said thick walled connection portion of at least one of said end piece members also comprising a convex portion, and said thick walled connection portion of at least one of said temple members also comprising a concave portion;

c. wherein, when said second end of each temple member is moved from the first position to the second position relative to said end piece members, the contact end surface of each of said temple members engage the contact end surface of said each of said first end piece members to form a first and second common joint portion, and the convex portion of said at least one end piece member is inserted into the concave portion of said at least one temple member to form a hermetic seal and establish air communication between said at least one end piece member and said at least one temple member and said first and second common joint portions are prevented from being damaged during use.

2. The oxygen breathing apparatus of claim 1, further comprising a first hinged joint associated with said first temple member and said first end piece member, and a second hinged joint associated with said second temple member and said second end piece member.

3. The oxygen breathing apparatus of claim 2, wherein said first and second hinged joints are spring biased.

4. The oxygen breathing apparatus of claim 1, wherein said first temple member is in air communication with said first end piece member and said second temple member is in air communication with said second end piece member.

5. The oxygen breathing apparatus of claim 1 wherein the tubular members comprise an eyeglass frame.

6. The oxygen breathing apparatus of claim 5, wherein the eyeglass frame comprises a pair of eyeglasses.

7. The apparatus of claim 6, wherein said second end of said second temple member comprises a third thick walled portion having a third contact end surface and a second concave portion, and said second end of said second end piece member comprises a fourth thick walled connection portion having a fourth contact end surface and a second convex portion, wherein when said second temple member and said second end piece member move from said first position to said second position said second convex portion is hermetically seated in said second concave portion, said third contact end surface contacts said fourth contact end surface, and said second temple member is in air communication with said second end piece member.

8. The apparatus of claim 5, wherein said second temple member and said second end piece member comprise hollow tubular members.

9. The apparatus of claim 5 further comprising a nostril cannula attached to said eyeglass frame and in air communication with said first end piece member.

10. The apparatus of claim 8 further comprising an air supply in air communication with said first end of said first temple member.

11. The apparatus of claim 5 wherein said eyeglass frame further comprises a pair of eyeglasses.

12. An oxygen breathing apparatus, comprising:

a. an eyeglass frame comprising first and second temple members and first and second end piece members, at least said first temple member and at least said first end piece member comprising hollow tubular members, said first and second temple members having first and second ends and said first and second end piece members having first and second ends;

b. a first hinged joint interconnecting the second end of said first temple member and the second end of said first end piece member, and a second hinged joint interconnecting the second end of said second temple member and the second end of said second end piece member, said temple members and said end piece members moving between a first position and a second position about said first and second hinged joints;

c. said second end of at least said first temple member comprising a first thick walled portion having a first contact end surface and a first concave portion, and said second end of at least said first end piece member comprising a second thick walled connection portion having a second contact end surface and a first convex portion;

d. wherein when said at least first temple member and said at least first end piece member move from said first position to said second position said convex portion is hermetically seated in said concave portion, said first contact end surface contacts said second contact end surface, and said first temple member is in air communication with said first end piece member.

13. The apparatus of claim 12, further comprising an air supply in air communication with said first ends of said first and second temple members and a nostril cannula in air communication with said first ends of said first and second end piece members.

* * * * *